United States Patent [19]

Dyott

[11] 4,154,529
[45] May 15, 1979

[54] SYSTEM FOR DETECTING REFLECTED LASER BEAMS

[75] Inventor: Richard B. Dyott, London, England

[73] Assignee: Andrew Corporation, Orland Park, Ill.

[21] Appl. No.: 779,361

[22] Filed: Mar. 21, 1977

[51] Int. Cl.$^2$ ............................................. G01D 3/36
[52] U.S. Cl. .................................... 356/28; 250/227; 356/342; 350/96.18
[58] Field of Search .................... 356/28, 5, 103, 207, 356/208; 350/96 C; 250/199, 227

[56] References Cited

U.S. PATENT DOCUMENTS

| | | | |
|---|---|---|---|
| 3,068,742 | 12/1962 | Hicks, Jr. et al. | 250/227 |
| 3,328,594 | 6/1967 | Sheldon | 250/227 |
| 3,511,227 | 5/1970 | Johnson | 356/28 |
| 3,556,659 | 1/1971 | Hawes | 356/103 |
| 3,867,033 | 2/1975 | Hasinger | 356/103 |
| 3,941,477 | 3/1976 | School | 356/28 |
| 3,953,131 | 4/1976 | Britz | 250/227 |
| 3,981,592 | 9/1976 | Williams | 350/96 C |
| 3,998,552 | 12/1976 | Stewart et al. | 356/103 |
| 4,012,149 | 3/1977 | Bouillie et al. | 350/96 C |

OTHER PUBLICATIONS

T. Tanaka et al., *Applied Optics*, vol. 14, No. 1, p. 189, Jan. 1970.
N. Clark et al., *Am. J. of Physics*, vol. 38, No. 5, p. 575, May 1970.

*Primary Examiner*—S. C. Buczinski
*Attorney, Agent, or Firm*—Leydig, Voit, Osann, Mayer & Holt, Ltd.

[57] ABSTRACT

A system for detecting a reflected light beam includes a source of coherent light such as a laser beam, an optical fiber spaced away from the source for receiving an incident beam of coherent light from the source at one end of the fiber, means for reflecting a portion of the incident beam back through at least a portion of the fiber to radiate a reflected beam which includes narrow angle signals having a beam width corresponding to that of the incident beam and wide angle signals having a beam width substantially wider than that of the incident beam, receiving means between the source and the optical fiber for receiving the reflected beam and having an optical aperture therein for transmitting the incident beam and the narrow angle signals in the reflected beam, and a projector lens between the receiving means and the optical fiber for directing the incident beam into the optical fiber and for directing the narrow angle signals in the reflected beam into the optical aperture of the receiving means. This system may be used as a velocimeter for determining the velocity of moving particles adjacent the opposite end of the optical fiber from the end that receives the incident light beam. The receiving means typically comprises a mirror for reflecting the wide angle portion of the reflected beam into a photoelectric transducer, or the receiving means may itself be a photoelectric transducer.

1 Claim, 4 Drawing Figures ured by directing the laser beam onto the particles and detecting the frequency change between the incident and reflected beams due to Brownian motion of the particles, which is a function of particle size. These techniques have been used previously to measure particle velocities and sizes, but not with the improved efficiencies or improved accuracies made possible by the present invention.

SYSTEM FOR DETECTING REFLECTED LASER BEAMS

DESCRIPTION OF THE INVENTION

The present invention relates generally to the art of fiber optics and, more particularly, to an improved system for detecting a reflected optical signal that is transmitted through the same optical fiber that transmits the incident signal. In specific applications, this invention relates to velocimeters using the Doppler effect to measure the velocity of moving particles, such as in blood flow, and to the measurement of the sizes of particles with Brownian motion.

It is a principal object of this invention to achieve improved efficiency in a system for detecting reflected optical signals from an optical fiber which transmits both the incident and reflected optical signals. In this connection, one specific object of the invention is to provide a highly efficient velocimeter using the Doppler effect on a reflected light beam to measure the velocity of moving particles.

Another specific object of the invention is to provide improved accuracy in a velocimeter that uses the Doppler effect on a reflected light beam to measure the velocity of moving particles.

It is a further object of the invention to provide an efficient system for measuring the sizes of particles with Brownian motion by analyzing the frequency spectrum of light scattered from such particles.

A still further object of the invention is to provide systems of the foregoing type which can be efficiently and economically fabricated.

Other objects and advantages of the invention will be apparent from the following detailed description and the accompanying drawings, in which.

While the invention will be described in connection with certain preferred embodiments, it will be understood that it is not intended to limit the invention to those particular embodiments. On the contrary, it is intended to cover all alternatives, modifications and equivalents as may be included within the spirit and scope of the invention as defined by the appended claims.

Figure 1:
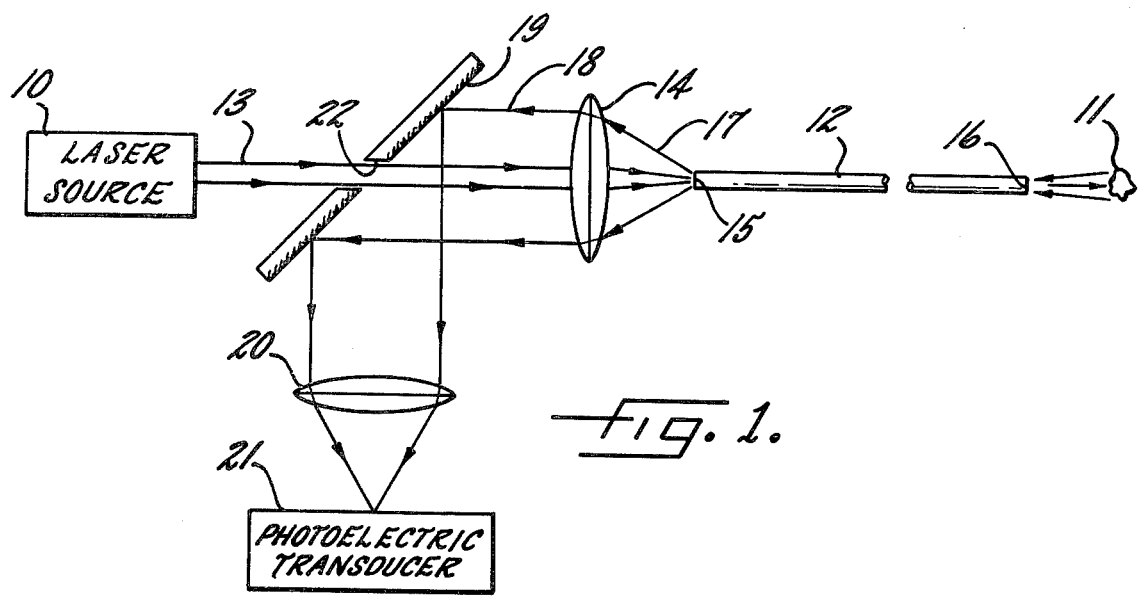
FIG. 1 is a schematic diagram of an optical system embodying the invention and suitable for use as a velocimeter.

Turning now to the drawings and referring first to FIG. 1, there is illustrated a system for using a laser beam source to determine the velocity and/or size of particles 11 located adjacent the end of an optical fiber 12. For example, this system can be utilized for in vivo measurements of blood flow by measuring the velocity of erythrocytes in a blood vessel, or to measure the velocity of liquid droplets in a flow of wet steam. Another application of the system is to measure the sizes of particles suspended in a liquid.

In general, the illustrative system measures velocities by directing the laser beam onto the moving particles and detecting the change in frequency between the incident laser beam and the reflected beam due to the Doppler effect, which is a function of the velocity of the particles. Particle sizes, on the other hand, are measured by directing the laser beam onto the particles and detecting the frequency change between the incident and reflected beams due to Brownian motion of the particles, which is a function of particle size. These techniques have been used previously to measure particle velocities and sizes, but not with the improved efficiencies or improved accuracies made possible by the present invention.

Returning now to FIG. 1, the laser beam source 10 generates an incident monochromatic laser beam 13 which is passed through a projector lens 14 and projected at a narrow angle into a first end 15 of the optical fiber 12.

Ideally the numerical aperture, NA, of the projector lens should be equal to, or slightly greater than, the NA of the optical fiber, which can be represented as follows:

$$NA \text{ fiber} = (n_1{}^2 - n_2{}^2)^{\frac{1}{2}},$$

where
$n_1$ = fiber core index
$n_2$ = fiber cladding index

The incident beam is transmitted through the fiber 12 to the second end 16 of the fiber where the beam emerges from the fiber and is reflected off the moving particles 11 under investigation. Motion of the particles 11 in a sense other than at right angles to the incident beam causes Doppler shift in the frequency of the beam reflected therefrom. That is, the frequency is increased if the particle is moving toward the fiber, and the frequency is reduced if the particle is moving away from the fiber.

The beam reflected from the particles 11 enters the end 16 of the fiber 12 at the full numerical aperture, i.e., at all angles up to the critical acceptance angle. The reflected beam travels through the optical fiber 12 and emerges from the first end 15 of the fiber at a much larger angle, i.e., a much larger beam width, than that of the incident light beam entering the fiber.

As the reflected beam leaves the fiber end 15, it passes through the projector lens 14 which converts the diverging beam 17 to a broad parallel beam 18 which is reflected transversely away from the path of the incident beam 13 by means of a mirror 19. More specifically, the mirror 19 is inclined at an angle of 45° C. to the axis of the incident beam 13, so that the broad beam 18 from the projector lens 14 is reflected perpendicularly away from the incident beam 13 to a detector lens 20. This lens 20 focuses the reflected beam onto a photoelectric transducer 21 which mixes the light reflected from the particles 11 with light reflected from the static far end 16 of the fiber and so produces an electrical signal whose frequency can be used to determine the velocity of the particles 11.

In accordance with an important aspect of the present invention, the mirror 19 has an optical aperture therein for transmitting the incident beam and the corresponding narrow angle portion of the reflected beam through the mirror. Thus, in the illustrative embodiment of the invention shown in FIG. 1, the mirror 19 has a physical opening 22 extending through the center thereof for passing the incident beam 13 from the source 10 to the projector lens 14, and for passing the corresponding narrow angle portion of the reflected beam 18 back toward the source 10. By providing this optical aperture 22 in the mirror 19, the remainder of the mirror can be made totally reflective so that it reflects all the optical energy impinging thereon. This is in contrast to the "half silvered" mirrors employed in prior art systems to permit bidirectional light transmission therethrough, at the cost of a 50% loss from both the incident and reflected signals. With the apertured mirror 19, a small fraction of the optical energy in the reflected beam 18 is lost through the aperture 22, but most of the energy in the reflected beam is reflected by the reflective portion of the mirror 19 to the detector lens 20. And there is no loss whatever from the incident beam 13 as it passes through the aperture 22. Consequently, the efficiency of the system provided by this invention is considerably greater than previous systems employing half-silvered mirrors.

Furthermore, in many applications of the illustrative system the reflected energy that is lost through the aperture 22 in the mirror 19 represents an unwanted fraction of the reflected beam, and thus the aperture also provides a valuable discrimination function. More specifically, the narrow angle portion of the reflected beam that is lost through the aperture 22 primarily comprises reflections of the incident beam from static surfaces rather than the moving particles 11, such as reflections from the projector lens 14 and the near end 15 of the optical fiber 12 on to which light is focused. Since it is only the reflections from the moving particles 11 that are subject to Doppler shift, the reflections from the static surfaces other than the far end 16 of the optical fiber generally represent unwanted signals and thus their loss through the aperture 22 is desirable to maximize the proportion of Doppler-shifted signals fed to the detecting transducer 21.

Unwanted reflections from the projector lens 14 and from the near end 15 of the optical fiber 12 may be further reduced by arranging for the source of light to be polarized and by placing a polarization filter in front of the photoelectric transducer 21 and positioning the filter so as to reject the unwanted light. Thus the reference signal may effectively be derived only from the light which is reflected from the far end 16 of the fiber. If the light reflected from both ends of the fiber 12 is received at the transducer 21, the two waves beat to give a resultant signal which depends on the magnitude and the phase of the waves at the detection surface of the transducer 21. Then if the fiber 12 is moved, the path difference between the reflections is changed slightly and, since the wavelength is so small, any slight change in the path length causes a large change in the phase difference $\phi$ between the two reflections. This produces a beat frequency $f_b$ $$f_b = d\phi/dt$$

By polarizing the light entering the fiber 12 and putting a crossed polarizer before the transducer 21, any light reflected from the entrance end 15 of the fiber (plus reflections from the lens surfaces) can be virtually eliminated. This ensures that the reference signal for beating against the Doppler-shifted signal (i.e. the "local oscillator" signal) comes only from the far end 16 of the fiber 12 where light is reflected to some extent because of the change in refractive index between fiber end 16 and the surrounding material (e.g., air or water). Thus there are no secondary beat signals due to the variation (mechanically induced) of the length of the fiber 12.

Since the reference signal is derived from the far end 16 of the fiber, the reflection, and therefore the reference signal, is zero when the fiber end 16 is immersed in a medium whose refractive index is equal to that of the fiber core. In that event a reference signal can be obtained by rotating the polarizer placed in front of the transducer 21 to allow some light reflected off the front end 15 of the fiber to pass through.

One of the advantages of the present invention is that such a reference signal is available in the reflected beam that arrives at the detecting transducer 21. Thus, although the narrow angle portion of the reflected light is lost through the aperture 22, the light that is reflected from the static surface at the far end 16 of the fiber 12 is sufficiently scattered that it also includes a certain amount of light reflected at a large enough angle to strike the reflective portion of the mirror 19. Consequently, the beam reflected by the mirror 19 to the detector 20 still includes a sufficient amount of light from a static surface to serve as a reference signal.

The efficiency of the illustrative system can be defined and calculated as follows:

Let $P_r$ = total power of light returned from the full numerical aperture of fiber.

$P_1$ = power lost through hole in mirror.

Then the efficiency may be defined as $$\frac{\text{Returned power detected}}{\text{Total returned power}} \eta$$

$$\eta = (P_r - P_1)/P_r$$

If D is the diameter of the returning beam just before it is reflected from the mirror, and d is the diameter of the hole in the mirror, then:

$$\eta = (P_r - P_1)/P_r = 1 - (d/D)^2$$

If f is the focal length of the projector lens 14 and $\theta_m$ is the maximum angle at which the reflected beam leaves the optical fiber 12:

$$D = 2f \operatorname{Tan}(\theta_m);$$

$$\theta_m = \operatorname{Sin}^{-1}(NA);$$

$$\eta = 1 - \left( \frac{d}{2f \operatorname{Tan}[\operatorname{Sin}^{-1}(NA)]} \right)^2$$

In a particular example with a fiber NA = 0.23 and a projector lens with f = 16 mm together with a mirror hole diameter d = 1 mm $$\eta = 1 - \left( \frac{1}{32 \operatorname{Tan}[\operatorname{Sin}^{-1}(.23)]} \right)^2 = 0.9825 \text{ or } 98.25\%$$

This compares with an efficiency of 0.25 or 25% for the half-silvered mirror system.

For any given frequency of the incident beam, there is some indeterminancy in the velocity determined from the frequency change fd in the reflected beam because there is a slight spread $\Delta fd$ in the frequency change fd in the reflected beam. This spread $\Delta fd$ is due to the fact that reflected light from a moving particle 11 can be accepted by the optical fiber 10 at any angle up to $\theta_m$. Then since $$fd = (2V/\lambda) \operatorname{Cos} \theta_m$$

V = Particle velocity $$\theta_m = \operatorname{Sin}^{-1}(NA)$$

λ = Wavelength of light in propagating medium
Δfd/fd = Normalized frequency spread = $1 - \cos[\sin^{-1}(NA)]$ This spread in frequency Δfd thus causes the indeterminacy in measuring velocities. For example, for a typical fiber NA=0.23:

$$\Delta fd/fd = 1 - \cos[\sin^{-1}(0.23)] = 0.027 \text{ or } 2.7\%$$

This means that the velocity determined from the frequency of the reflected beam can be in error by as much as 2.7%, which is tolerable for many measurement applications.

Figure 2:
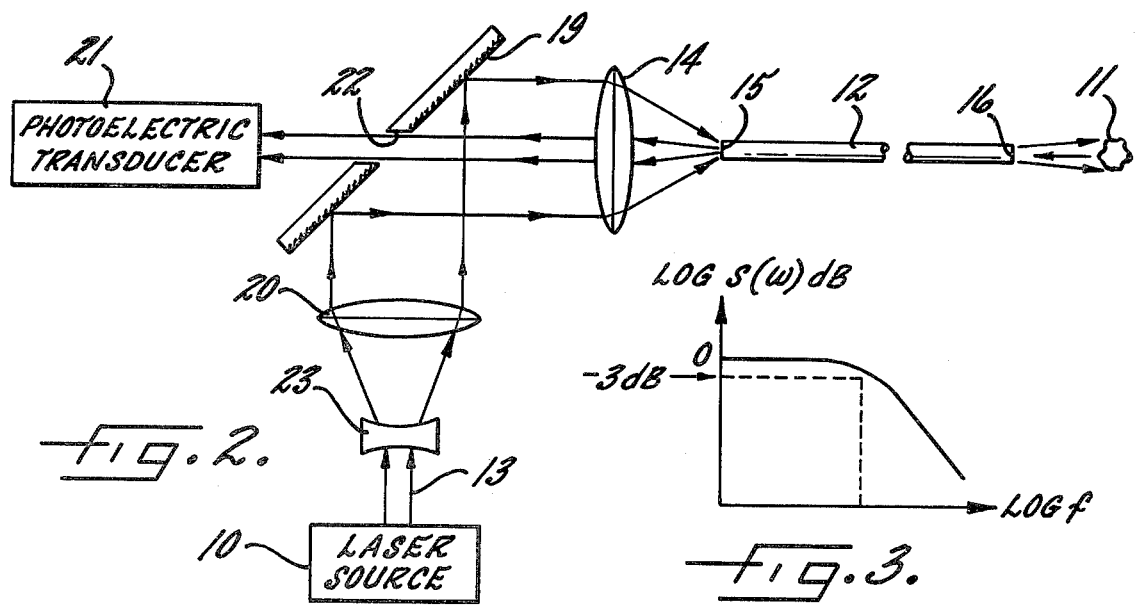
FIG. 2 is a schematic diagram of an alternative embodiment of the invention.

In FIG. 2, there is shown a modified embodiment of the invention that can be used for more precise velocity measurements, at a sacrifice in efficiency. This arrangement uses the apertured mirror to reflect the incident beam rather than the reflected beam so that the narrow angle energy that is lost through the aperture is derived from the incident beam rather than the reflected beam.

Thus, the positions of the detecting transducer 21 and the laser source 10 are interchanged in the system of FIG. 2, and a concave lens 23 is added to broaden the incident beam 13 to the diameter of the projector lens 14. The lens 20 receives the broadened beam from the lens 23 and collimates it before it is directed onto the mirror 19. Although a small fraction of the incident beam is lost through the aperture 22 in the mirror 19, most of the incident beam generated by the source 10 is reflected by the mirror 19 through the projector lens 14 and into the optical fiber 12.

While the reflected beam emerging from the first end 15 of the optical fiber 12 is the same as that described above in the system of FIG. 1, only that portion of the reflected beam near the axis of the optical fiber passes through the aperture 22 and on to the detecting transducer 21. The balance of the reflected beam strikes the mirror 19 and is returned to the source 10, where it is lost. Thus, the only optical signals which reach the detecting transducer 21 are those which are transmitted through the optical fiber 10 at very small angles to the fiber axis, and as a result there is very little spread in the frequency change in the reflected beam and the resultant velocity measurement. This system is particularly useful for making a highly accurate determination of the velocity of axial flow in liquids or gases by investigating the velocity of particles therein, e.g., the velocity of erythrocytes in in vivo measurements of blood flow, or droplets of water in wet steam.

The improved accuracy of the system shown in FIG. 2 is achieved at the expense of an enormous reduction in efficiency. For example, in a system having the exemplary dimensions described above, the efficiency is reduced from 98.25% to 1.72%. This efficiency reduction is, of course, caused by the fact that detection of the reflected beam is limited to only that portion of the beam transmitted near the axis of the optical fiber. Thus, if:

$P_t$ = total power from laser.
$P_1$ = power incident on the inner end of the fiber.

$$P_i = P_t - P_t(d/D)^2;$$

$$P_r = [P_t - P_t(d/D)^2](d/D)^2$$

$$\eta = [1 - (d/D)^2](d/D)^2$$

For the previous example the efficiency is now
$\eta = 0.9825(1 - 0.9825) = 0.0172$ or 1.72%

Another application for the system of this invention is measurement of the diameter of particles suspended in a liquid by analysis of the frequency spectrum S(ω) of light scattered from the particles with Brownian motion. The diffusion constant D for such particles is related to the particle radius a, the temperature T, and the viscosity η of the liquid by the Stokes-Einstein relation, as follows:

$$D = kT/6\pi\eta a \tag{1}$$

where k is Boltzmann's constant.

Figure 3:
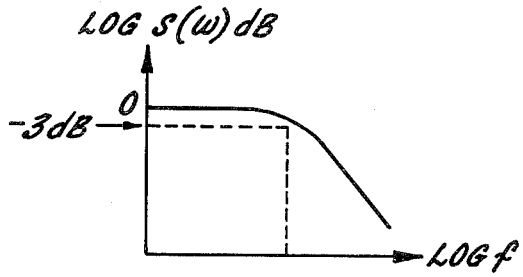
FIG. 3 is a graph of Log S ($\omega$) versus Log f for an exemplary analysis made by the system of FIG. 1.

The frequency spectrum S(ω) of light scattered from particles with Brownian motion is given by:

$$S(\omega) \alpha \frac{\Gamma(\theta)}{[\omega^2 + \Gamma(\theta)]} \tag{2}$$

where ω = radian frequency = 2πf $$\Gamma(\theta) = D\left(\frac{4\pi n}{\lambda_o} \sin \theta/2\right)^2 \tag{3}$$

and n = refractive index of the liquid
$\lambda_o$ = free space wavelength
θ = scattering angle If a plot is made of Log S(ω) against Log ω or Log f, e.g., by using the dB and Log f scales on a spectrum analyzer, the resulting curve appears as shown in FIG. 3. At the −3 dB or half power point of S(ω)

$$\omega^2 = \Gamma^2(\theta) \tag{4}$$

Then:

$$\omega = D[4\pi n/\lambda_o] \sin(90°))^2 \tag{5}$$

Since ω is known from the analysis, this equation can be solved for D, and then equation (1) can be solved for a. θ/2 is taken to be 90° although the fiber will accept angles θ/2±φ where φ = $\sin^{-1}$(NA), NA = Numerical aperture. For strict accuracy an average should be taken over the angle of acceptance, but the correction factor Sinφ/φ will be near unity for the low numerical apertures used in the system of this invention. For example, for a numerical aperture of 0.15, the correction factor is:

0.15/$\sin^{-1}$ 0.15 = 0.996, or 99.6%

Thus, it can be seen that the velocity measurements made with the system of FIG. 2 will be 99.6% accurate.

Figure 4:
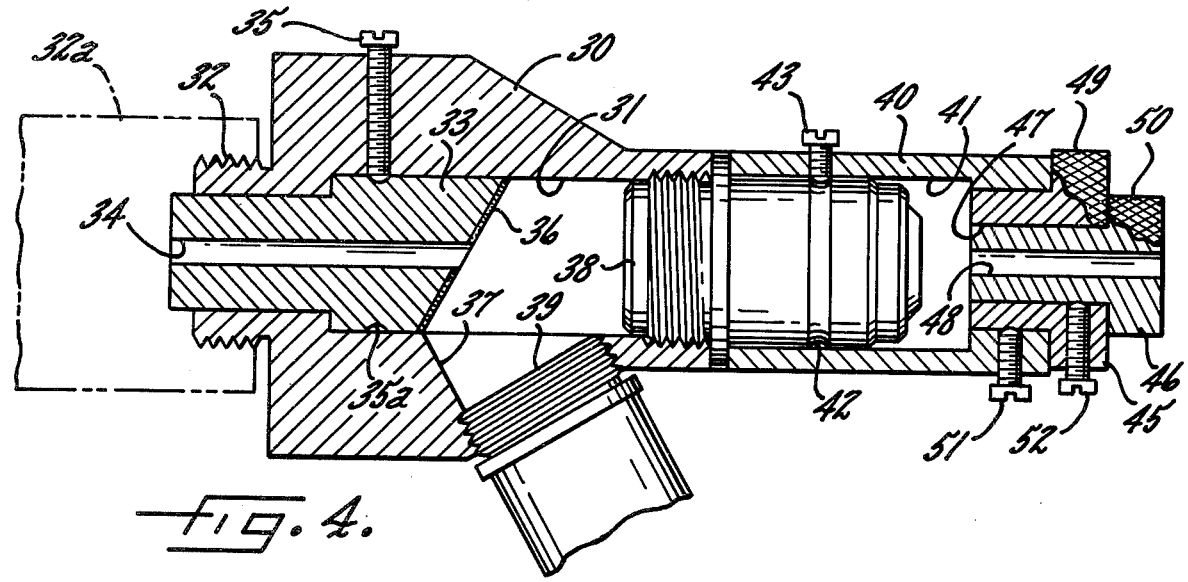
FIG. 4 is a longitudinal section of a device representing a preferred physical form of the system of FIG. 1.

Turning next to FIG. 4, there is shown an actual physical embodiment of a device embodying a major portion of the system illustrated in FIGS. 1 or 2, adapted for attachment to a laser source, an optical fiber, and a photoelectric detector including a focusing lens and transducer. Thus, the holder 30 in FIG. 4 is formed with a central stepped cylindrical bore 31, the narrow part of which terminates in an externally threaded ferrule 32 for connecting the holder 30 to a laser source 32a. The bore 31 houses a thick-walled cylinder 33 of polymethylmethacrylate, the bore 34 of which is coaxial with the holder bore 31. This cylinder 33 is held by a side screw 35 threaded into a radial bore in the holder 30 and engaging a circumferential groove 35a in the cylinder 33. The outer or left-hand face of the cylinder 33 is perpendicular to its axis, but the inner face is inclined at 30° to its axis and is bright-aluminized to form a mirror 36 around the end of the bore 34. Thus, the laser beam from the source 32a is transmitted through the bore 34 and the mirror 36 to the projector lens to be described below.

For mounting a photodetector in the proper orientation to receive reflected light from the mirror 36, a branch bore 37 is formed in the holder 30 to intersect the central bore 31, the axis of the bore 37 being aligned with the axis of the bore 34 of the cylinder 33. The right-hand end of the holder bore 31 and the outer end of the branch bore 37 are of equal diameter and are internally threaded for the reception and interchangeability of lens holders 38 and 39.

The lens holder 38 projects into a housing 40 forming a central, cylindrical stepped bore 41. The lens holder 38 is provided with a circumferential groove 42 by which the holder 38 is retained by a side screw 43 threaded through a radial bore in the housing 40.

The narrower part of the central bore 41 in the housing 40 supports a nesting pair of cylindrical adjusters 45, 46 having eccentric longitudinal bores 47, 48, respectively, and knurled shoulders 49, 50 by which the adjusters are rotatable relative to each other and to the bore 41 to align the bore 48 of the radially inner adjuster 46 with the principal axis of the projector lens. The bore 48 is for supporting an optical fiber. The adjusters 45, 46 are held in position by respective side screws 51, 52 threaded through radial bores in the housing 40 and the adjuster 45, respectively.

As can be seen from the foregoing detailed description, this invention provides an extremely high degree of efficiency and/or accuracy in a system for measuring particle velocities or sizes by analyzing reflected optical signals from an optical fiber which transmits both the incident and reflected optical signals. The system is capable of achieving efficiencies as high as 98 to 99%, or accuracies as high as 99%. Furthermore, the system is sufficiently simple from a structural standpoint that it can be efficiently and economically fabricated.

I claim as my invention:

1. In a velocimeter, the improvement comprising
   (a) a source of coherent light,
   (b) an optical fiber spaced away from said source for receiving an incident beam of coherent light from said source at a first end of the fiber and directing said light onto moving objects located adjacent a second end of the fiber, whereby said moving objects reflect a portion of said light back into said fiber with a beamwidth substantially wider than that of the incident beam so that the light reflected from said objects emerges from said first end of said fiber with a larger angle than that of the incident light beam entering the fiber, said second end of said fiber also reflecting a portion of the incident beam to produce reflected light emerging from said first end of said fiber with a larger angle than that of the incident beam entering said fiber,
   (c) a mirror between said source and said optical fiber for directing the wide angle reflected light emerging from the first end of said fiber transversely away from said incident beam, said mirror having an optical aperture therein for transmitting therethrough the incident beam,
   (d) a lens for directing the incident beam into the optical fiber,
   (e) and a photoelectric transducer for receiving the beam reflected by said mirror and converting said beam to analogous electrical signals.

* * * * *